(12) United States Patent
Isshiki et al.

(10) Patent No.: US 11,523,908 B2
(45) Date of Patent: Dec. 13, 2022

(54) DYSPHONIA TREATMENT TOOL

(71) Applicant: NOBELPHARMA CO., LTD., Tokyo (JP)

(72) Inventors: Nobuhiko Isshiki, Shiga (JP); Takako Aburada, Tokyo (JP)

(73) Assignee: NOBELPHARMA CO., LTD., Tokyo (JP)

( * ) Notice: Subject to any disclaimer, the term of this patent is extended or adjusted under 35 U.S.C. 154(b) by 742 days.

(21) Appl. No.: 16/475,318

(22) PCT Filed: Dec. 29, 2016

(86) PCT No.: PCT/JP2017/047358
§ 371 (c)(1),
(2) Date: Jul. 1, 2019

(87) PCT Pub. No.: WO2018/124301
PCT Pub. Date: Jul. 5, 2018

(65) Prior Publication Data
US 2019/0328531 A1    Oct. 31, 2019

(30) Foreign Application Priority Data

Dec. 29, 2016 (JP) .............................. JP2016-257375
Aug. 24, 2017 (JP) .............................. JP2017-160944

(51) Int. Cl.
*A61F 2/30* (2006.01)
*A61F 2/46* (2006.01)
*A61F 2/20* (2006.01)

(52) U.S. Cl.
CPC ...... *A61F 2/30756* (2013.01); *A61F 2/30749* (2013.01); *A61F 2002/30754* (2013.01)

(58) Field of Classification Search
None
See application file for complete search history.

(56) References Cited

U.S. PATENT DOCUMENTS

| | | | |
|---|---|---|---|
| 4,130,905 A | 12/1978 | Mercandino | |
| 5,860,977 A | 1/1999 | Zucherman et al. | |
| (Continued) | | | |

FOREIGN PATENT DOCUMENTS

| | | |
|---|---|---|
| CN | 1246041 | 3/2000 |
| CN | 2933336 Y | 8/2007 |
| (Continued) | | |

OTHER PUBLICATIONS

Sanuki, et al., "Surgical treatment for adductor spasmodic dysphonia—mainly focusing on surgical technique of Thyroplasty type II", Isshiki Clinic for Plastic Surgery and Otolaryngology (Kyoto Voice Surgery Center), Nose and Ear and Clinical Practice, vol. 51, No. 5, 2005, pp. 381-386—Abstract.

(Continued)

*Primary Examiner* — Ann Schillinger
(74) *Attorney, Agent, or Firm* — Hamre, Schumann, Mueller & Larson, P. C.

(57) ABSTRACT

Object:
Provided is a dysphonia treatment tool in which a front surface piece is bent.
Resolution means:
A dysphonia treatment tool includes a plurality of clamping sections (1, 1) each including a front surface piece (1a) disposed from a cut end surface of thyroid cartilage incised to a front surface, and a rear surface piece (1b) disposed on a rear surface of the thyroid cartilage, and being fitted respectively to cut ends of the thyroid cartilage that are opposite each other, and a bridging section (2) linking the plurality of clamping sections (1, 1) to each other. The front surface piece (1a) is bent in an intermediation section between a base end and a distal end of the front surface piece (1a).

6 Claims, 5 Drawing Sheets

(56) References Cited

U.S. PATENT DOCUMENTS

| | | | |
|---|---|---|---|
| 7,090,697 B2 * | 8/2006 | Isshiki | A61F 2/20 623/9 |
| 7,997,266 B2 * | 8/2011 | Frazier | A61F 2/82 128/207.14 |
| 10,813,765 B2 * | 10/2020 | Sanuki | A61F 2/30749 |
| 2004/0254642 A1 * | 12/2004 | Isshiki | A61F 2/20 623/9 |
| 2006/0150986 A1 * | 7/2006 | Roue | A61F 2/04 128/848 |
| 2008/0294011 A1 * | 11/2008 | McLoughlin | A61B 17/0293 600/210 |
| 2011/0288655 A1 * | 11/2011 | Belafsky | A61B 90/00 623/23.64 |
| 2011/0301580 A1 | 12/2011 | Hoffman | |
| 2018/0228611 A1 | 8/2018 | Sanuki et al. | |
| 2020/0330219 A1 * | 10/2020 | Abu | A61F 2/20 |

FOREIGN PATENT DOCUMENTS

| | | | |
|---|---|---|---|
| JP | 2005-000330 | 1/2005 | |
| WO | 2015/111340 | 7/2015 | |
| WO | WO-2015111340 A1 * | 7/2015 | A61B 17/24 |
| WO | 2016/002924 | 1/2016 | |
| WO | WO-2016002924 A1 * | 1/2016 | A61B 17/02 |
| WO | 2017/026493 | 2/2017 | |

OTHER PUBLICATIONS

Isshiki, et al., "Surgical tips for type II thyroplasty for adductor spasmodic dysphonia: modified technique after reviewing unsatisfactory cases", Acta Oto-Laryngologica, 2010; 130:275-280.

Isshiki, et al., "How to Decide Indication of Type 2 Thyroplasty for Spasmodic Dysphonia", The Larynx Japan, vol. 23, No. 1, Jan. 1, 2011, pp. 1-7—Abstract.

International Search Report issued in International Application No. PCT/JP2017/047358, dated Jun. 12, 2018, 1 page.

Written Opinion issued in International Application No. PCT/JP2017/047358, dated Jun. 12, 2018, 6 pages.

Extended European Search Report issued in European Patent Application No. 17885926.0, dated Aug. 10, 2020, 36 pages.

Office Action issued in corresponding Chinese Patent Application No. 201780067852.4, dated Sep. 24, 2020, 10 pages w/translation.

Search Report issued in corresponding Chinese Patent Application No. 201780067852.4, dated Sep. 17, 2020, 2 pages.

Office Action issued in corresponding Chinese Patent Application No. 201780067852.4, dated Apr. 16, 2021, 11 pages w/translation.

* cited by examiner

DYSPHONIA TREATMENT TOOL

TECHNICAL FIELD

The present invention relates to a dysphonia treatment tool.

BACKGROUND ART

To improve spasmodic dysphonia such as a condition in which vocal cords fail to vibrate due to excessive glottic closure, there has been proposed a dysphonia treatment tool described in Patent Document 1 below. The dysphonia treatment tool disclosed in Patent Document 1 includes two clamping sections made from titanium and clamping cut ends on both sides of incised thyroid cartilage (so-called Adam's apple), and a bridging section made from titanium and bridging the two clamping sections to maintain an incision space of the incised thyroid cartilage. The clamping sections each include a front surface piece disposed on a front surface side of the incised thyroid cartilage, and a rear surface piece disposed on a rear surface side of the thyroid cartilage.

To use this treatment tool, the thyroid cartilage is incised in the center, the cut ends of the thyroid cartilage are separated by forceps, the clamping sections are fit to the cut ends separated and being opposite each other, and the forceps are removed. Then, the separated cut ends elastically return in a closing direction, and thus the treatment tool is securely fixed between the cut ends.

Further, a suture thread is caused to pass through holes formed at positions near the bridging section of the front surface pieces for the purpose of gripping the treatment tool or the like, and the treatment tool and the thyroid cartilage are sewed together. As a result, displacement of the set treatment tool at the cut ends is more reliably prevented. According to the above, the treatment tool can be fixed reliably between the separated thyroid cartilage.

CITATION LIST

Patent Literature

Patent Document 1: JP 2005-330 A

SUMMARY OF INVENTION

Technical Problem

Thyroid cartilage has a shape projecting to a front surface side of a neck in a tapered manner. In addition, a projection angle of thyroid cartilage differs depending on sex, race, and the like.

Therefore, when the dysphonia treatment tool described in Patent Document 1 is disposed to thyroid cartilage, there has been a problem in that the treatment tool is not necessarily attached as illustrated in FIG. 3 in Patent Document 1 and that, in particular, a part of the front surface piece from the vicinity of the center to the distal end side floats from the thyroid cartilage.

Thus, an object of the present invention is to provide a dysphonia treatment tool including a front surface piece easily extending along thyroid cartilage.

Solution to Problem

A dysphonia treatment tool according to the present invention includes a plurality of clamping sections each including a front surface piece disposed from a cut end surface of thyroid cartilage incised to a front surface, and a rear surface piece disposed on a rear surface of the thyroid cartilage, and being fitted respectively to cut ends of the thyroid cartilage that are opposite each other, and a bridging section linking the plurality of clamping sections to each other. The front surface piece is bent to a rear surface piece side in an intermediation section between a base end and a distal end of the front surface piece.

In the present invention, the bending part is provided in the intermediation section between the base end and the distal end of the front surface piece, and hence the treatment tool is easily disposed in conformity of a shape of thyroid cartilage.

In the present invention, the front surface piece may have a bending angle of equal to or greater than 10 degrees and equal to or less than 50 degrees.

When the bending angle is equal to or greater than 10 degrees and equal to or less than 50 degrees, fined adjustment can be performed easily at the bending part, and a width of the fine adjustment can be suppressed as much as possible.

Note that the bending angle refers to an angle formed by flat plates adjacent to each other sandwiching the bent part.

In the present invention, a part of the front surface piece that is disposed on the front surface of the thyroid cartilage may have a thickness dimension set to be equal to or greater than 0.05 mm and equal to or less than 0.6 mm, and the bending angle of the front surface piece may be formed to be changeable.

When the part of the front surface piece that is disposed on the front surface of the thyroid cartilage has a thickness of equal to or greater than 0.05 mm and equal to or less than 0.6 mm, the part can be bent easily.

In the present invention, the front surface piece of the dysphonia treatment tool may be bent smoothly.

When the front surface piece is smoothly bent, strangeness in appearance or sensory discomfort can be suppressed, and the dysphonia treatment tool can be fitted in easily at the time of attaching to the thyroid cartilage.

In the present invention, the front surface piece of the dysphonia treatment tool may be bent to form a corner portion.

When the front surface piece is bent to form a corner portion, the bending angle of the front surface piece becomes grasped easily.

In the present invention, a hole passing through the front surface piece in a thickness direction may be formed in the front surface piece, and the front surface piece may be bent with a position at which the front surface piece does not overlap with the hole being as a center.

Since the hole formed in the front surface piece and the bending center are away from each other, stress caused by bending can be prevented from being concentrated in the periphery of the hole.

In the present invention, a plurality of holes may be formed in one front surface piece, and the front surface piece may be bent with a part between the plurality of holes being as a center.

Since the center of bending is between the holes formed in the front surface piece, stress caused by bending is prevented from being concentrated in the peripheries of the holes.

In the present invention, the front surface piece of each of the plurality of clamping sections linked by the bridging section may be further bent to the rear surface piece side on a base end side with respect to a position at which the front surface piece is bent in an intermediation section between the base end and the distal end.

Advantageous Effects of Invention

The dysphonia treatment tool according to the present invention exerts an effect of easily extending along thyroid cartilage.

DESCRIPTION OF EMBODIMENTS

With reference to the drawings, an embodiment of a dysphonia treatment tool according to the present invention will be described.

Figure 1:
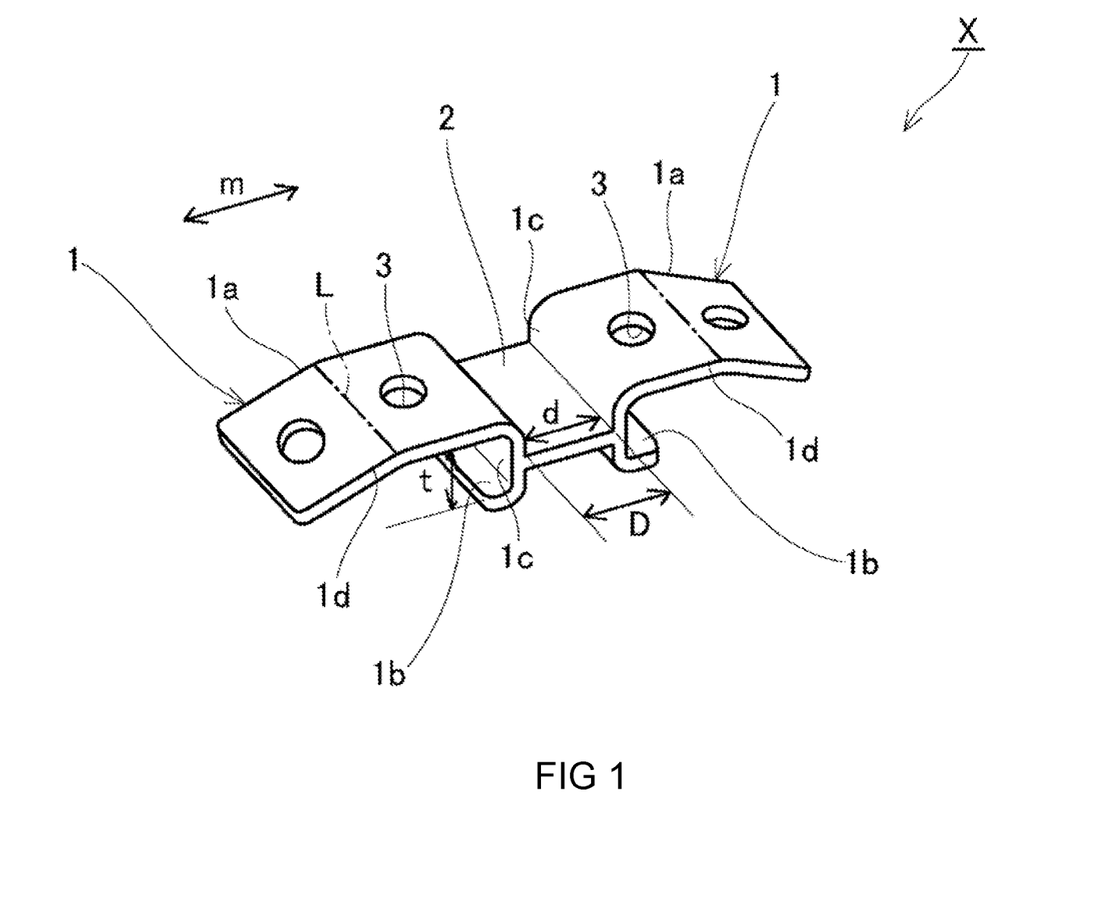
FIG. 1 is a perspective view illustrating a dysphonia treatment tool according to an embodiment of the present invention.

As illustrated in FIG. 1, a dysphonia treatment tool (hereinafter referred to as a "treatment tool") X according to an embodiment of the present invention includes a plurality (one set of one pair in the present embodiment) of clamping sections 1, 1 each including a front surface piece 1a and a rear surface piece 1b, and being fit respectively to cut end surfaces 12a, 12a of thyroid cartilage 11 incised illustrated in FIG. 3 that are opposite each other, and a bridging section 2 linking the plurality of clamping section 1, 1 to each other.

Figure 2:
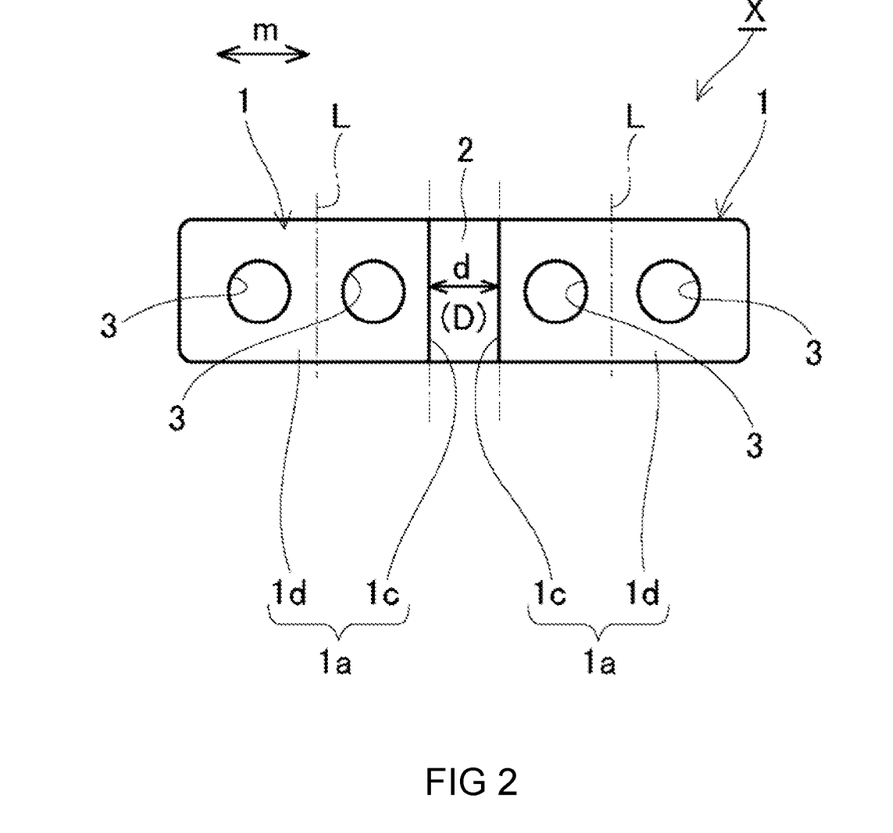
FIG. 2 is a plan view of the dysphonia treatment tool according to the embodiment of the present invention.

As illustrated in FIG. 2, the front surface piece 1a is formed into a substantially strip-like plate shape in a planar view. A part on a base end side in a longitudinal direction m of the front surface piece 1a forms an end surface section 1c that is bent and brought into contact with the cut end surface 12a of the thyroid cartilage 11 illustrated in FIG. 3. As illustrated in FIG. 1, a part on the distal end side of the front surface piece 1a with respect to the end surface section 1c forms a front surface contacting section 1d that is brought into contact with a front surface 11a of the thyroid cartilage 11 illustrated in FIG. 3.

A plurality (two in the present embodiment) of holes 3 are formed in the front surface contacting section 1d of the front surface piece 1a at an interval in the longitudinal direction m. A suture thread (not illustrated; hereinafter the same) can be inserted through these holes 3, 3, and these holes 3, 3 are each formed to have a diameter dimension of from 1.0 mm to 2.0 mm to enable the suture thread to pass through.

An intermediate section between the distal end side and the base end side of the front surface contacting section 1d is bent to the rear surface piece 1b side to be curved with an imaginary line L being as a center. The imaginary line L is at a substantially center between the holes 3, 3, and crosses (substantially orthogonal in the present embodiment) an array direction of the holes 3, 3. In addition, the bending is performed at a position not overlapping with the holes 3 on the imaginary line L being the substantially center of the curve.

The bending of the front surface contacting section 1d may be formed in advance at the time of manufacturing the front surface piece 1a, or may be formed by a jig or other means before treatment.

A bending angle of the front surface contacting section 1d may be set to be equal to or greater than 10 degrees and equal to or less than 50 degrees, preferably set to be equal to or greater than 25 degrees and equal to or less than 45 degrees, and more preferably set to be equal to or greater than 30 degrees and equal to or less than 45 degrees.

A thickness dimension of the front surface contacting section 1d of the front surface piece is set to be equal to or greater than 0.05 mm and equal to or less than 0.6 mm, and the end surface section 1c is formed to be thicker than the front surface contacting section 1d.

Note that the bending angle refers to an angle formed by flat plates adjacent to each other sandwiching the bent part.

Figure 3:
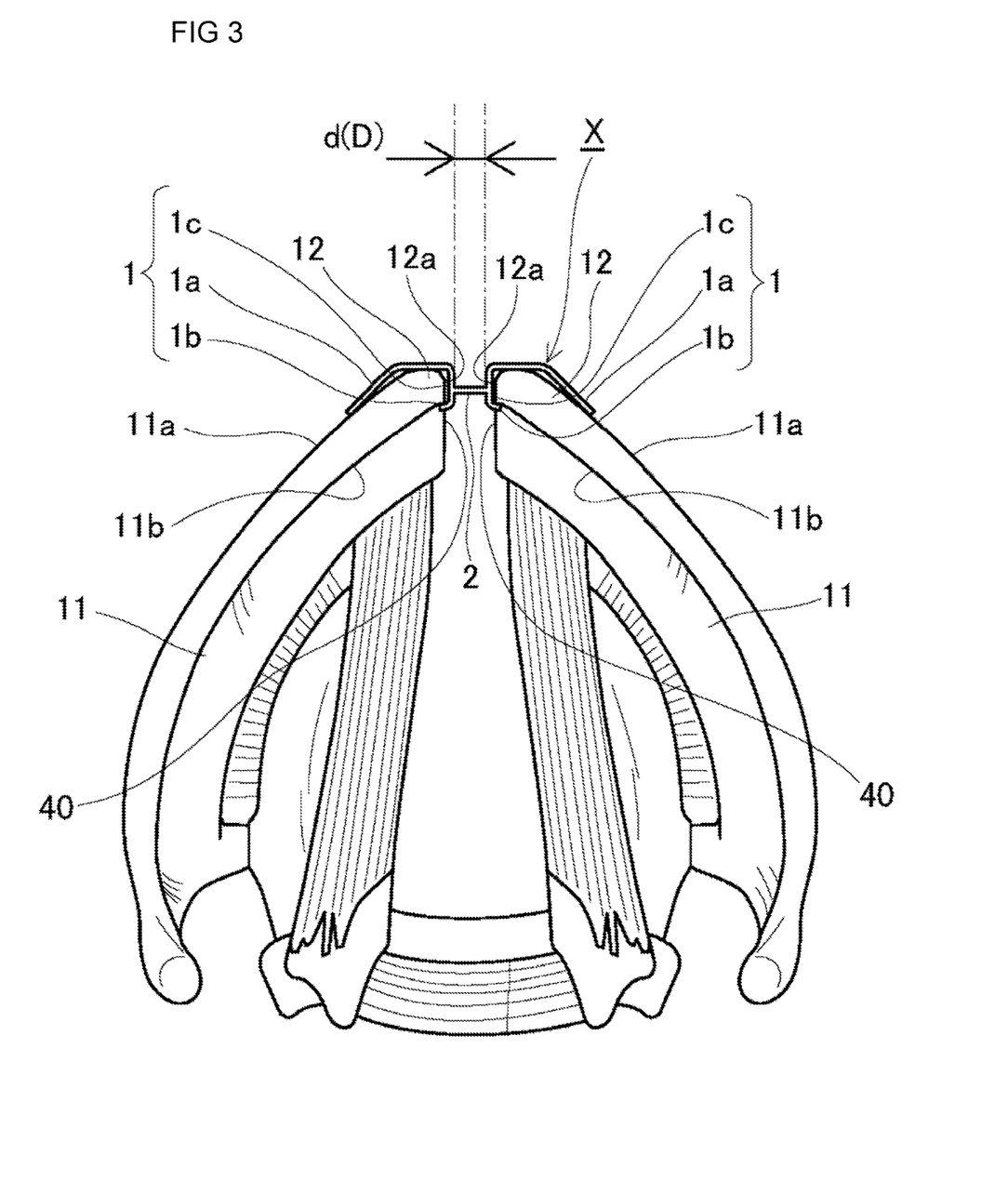
FIG. 3 is a view illustrating a state in which the dysphonia treatment tool according to the embodiment of the present invention is set to thyroid cartilage.

The rear surface piece 1b is a section that is bent to extend from the end surface section 1c of the front surface piece 1a toward a rear surface 11b side of the thyroid cartilage 11 illustrated in FIG. 3.

The front surface piece 1a and the rear surface piece 1b are integrally formed to constitute the clamping section 1.

In the clamping section 1, a length of the front surface contacting section 1d is a necessary and sufficient length for clamping the thyroid cartilage 11, and may be such length that can extend along a form of the thyroid cartilage 11. Specifically, it is preferred that the length be set to from about 8 mm to about 12 mm. In addition, it is preferred that the rear surface piece 1b have a length enabling contact from an end edge of the cut end (end) 12 of the thyroid cartilage 11 to an end edge of a soft tissue 40 located below the thyroid cartilage 11, and specifically, the rear surface piece 1b have a length of from about 1.5 mm to about 3.5 mm.

The right and left pair of clamping sections 1 are provided substantially symmetrically such that the front surface piece 1a is disposed on the front surface 11a side of the thyroid cartilage 11 and the cut end surface 12a, and the rear surface 1b is disposed on the rear surface 11b side of the thyroid cartilage 11, and as a result, the clamping sections 1 can be fitted respectively to the cut ends (ends) 12, 12 of the thyroid cartilage 11 that are opposite each other. In addition, the pair of clamping sections 1, 1 are linked by the bridging section 2. The bridging section 2 is a section that links the clamping sections 1, and links the clamping sections 1 in an intermediate section in an extending direction of the end surface section 1c. A length (d) of the bridging section 2, that is, a space D between both of the clamping sections 1, 1, is equivalent to a distance between the cut ends 12, 12 of the thyroid cartilage 11 separated and, while the length (d) differs in accordance with symptoms, body types, and voice states of patients with dysphonia, the length (d) is generally set within the range from 2 to 6 mm.

In addition, the bridging section 2 has a thickness greater than a thickness of the front surface contacting section 1d of the front surface piece 1a, and is formed to have a thickness equivalent to a thickness of the end surface section 1c.

The clamping sections 1 and the bridging section 2 are both made from titanium. A titanium metal used in the present invention is not limited to titanium as a pure metal, and includes a titanium alloy used in an artificial bone, an artificial joint, and a dental implant as a biomedical metal material. Specifically, Ti-6Al-4V that does not contain Ni identified as a cause of cancer and allergies, and that is known as a titanium alloy excellent in biocompatibility, or the like can be used. To prevent wear and elution, the titanium or the titanium alloy may be injected with N or C ions to modify a surface.

As illustrated in FIG. 1, it is preferred that a space (extending dimension of the end surface section 1c) t between the front surface contacting section 1d and the rear surface piece 1b be slightly greater than a thickness dimension of the thyroid cartilage 11, and specifically it is preferred that the space t be from about 2 to about 4 mm. When the space t is less than the thickness dimension of the thyroid cartilage 11 illustrated in FIG. 3, the thyroid cartilage 11 is squeezed, and the clamping sections 1 continually apply pressure on the thyroid cartilage 11 for a long period of time, and there is a possibility of erosion and damage to the thyroid cartilage 11. On the other hand, when the space t between the front surface contacting section 1d and the rear surface piece 1b is excessively large as compared to the thickness dimension of the thyroid cartilage 11, the thyroid cartilage 11 becomes substantially difficult to clamp, and the clamping sections 1 become relatively more susceptible to position shifting (sliding) with respect to the thyroid cartilage 11.

Next, a method of forming the thyroid cartilage 11 suitable for vocalization (treatment method for dysphonia) with use of the treatment tool X according to the present invention will be described.

To form the thyroid cartilage 11 suitable for vocalization with use of the treatment tool X according to the present invention, a method including a space measuring step of measuring a space suitable for vocalization, a disposing step of disposing the treatment tool X, and a fitting step of clamping the clamp sections 1, 1 may be applied. At the space measuring step, as illustrated in FIG. 3, the thyroid cartilage 11 is incised in the center section, a space between the cut ends 12, 12 of the thyroid cartilage 11 incised is separated, and a space suitable for vocalization is measured. At the disposing step, a space between the cut ends 12, 12 is separated to be slightly larger than the measured space, and the treatment tool X is disposed such that, between the cut ends 12, 12, the rear surface pieces 1b, 1b of the treatment tool X extend along the rear surface 11b of the thyroid cartilage 11 and that the distal end sides and/or the base end sides with the bent parts of the front surface contacting sections 1d, 1d of the treatment tool X, as boundaries, extend along the front surface 11a of the thyroid cartilage 11. At the fitting step, the cut ends 12, 12 clamp the clamping section 1, 1 right and left such that the cut ends 12, 12 separated are opened and the space between the cut ends 12, 12 can be maintained.

In this method, though it is not necessary, a method further including a suturing step may be applied. At the suturing step, the cut ends 12, 12 clamp the clamping sections 1, 1 right and left, and subsequently, a suture thread is caused to pass through the hole 3 formed in the front surface piece 1a, and the front surface piece 1a and the cut end 12 of the thyroid cartilage 11 are fixed with the suture thread.

In addition, in each method described above, though it is not necessary, the method may further include a shape measuring step of measuring a shape of the thyroid cartilage 11 of a patient in advance. At the disposing step and the fitting step, more preferably the treatment tool X that is shaped in conformity with the measured shape of the thyroid cartilage 11 is used.

The shape of the thyroid cartilage 11 of a patient can be measured by, for example, a multi-slice helical CT method and an MRI method.

Specifically, first, as illustrated in FIG. 3, the thyroid cartilage 11 is incised in the center section, and a space between the cut ends 12, 12 for vocalization improvement is measured while urging the patient to vocalize (space measuring step).

After the space to separate is determined, the treatment tool X having the length d of the bridging section 2 in conformity with the space is selected, and the clamping sections 1 are disposed between the cut ends 12, 12 such that the front surface piece 1a is brought into contact with the front surface 11a and the cut end 12a of the thyroid cartilage 11 and the rear surface piece 1b is brought into contact with the rear surface 11b of the thyroid cartilage 11 (disposing step).

Then, the cut ends 12, 12 separated are opened, the cut ends 12, 12 clamp the treatment tool X by utilizing returning force by which the cut ends 12, 12 returns to the original closed state, and the thyroid cartilage 11 is fixed in the measured space (fitting step). Here, distal ends of the rear surface pieces 1b are inserted between the thyroid cartilage 11 and the soft tissue 40 located below the thyroid cartilage 11 such that the treatment tool X is attached to the thyroid cartilage 11 clamped by the clamping sections 1. In the treatment tool X according to the present invention, the rear surface pieces 1b are formed by a thin plate of titanium, and hence distal end sections of the rear surface pieces 1b can be inserted relatively easily between the thyroid cartilage 11 and the soft tissue 40.

The front surface contacting section 1d of the front surface piece 1a is bent in the intermediation section in the longitudinal direction m in advance to extend easily along the shape of the thyroid cartilage 11. Hence, the treatment tool X according to the present invention is fitted in conformity of shapes of the cut ends 12 of the thyroid cartilage 11.

When the front surface contacting section 1d is difficult to extend along the front surface 11a of the thyroid cartilage 11, the bending of the front surface contacting section 1d may be finely adjusted to match with the shape of the thyroid cartilage 11 (adjusting step) before disposing the treatment tool X between the cut ends 12, 12, or after temporarily removing the treatment tool X disposed from the cut ends 12, 12. In this case, the front surface contacting section 1d is bent in advance, and hence the bending angle at the bent part becomes easily adjusted.

In this manner, the treatment tool X is fitted to maintain with the treatment tool X the space between the cut ends 12, 12 of the thyroid cartilage 11 for satisfactory vocalization. Then, the other tissues are returned to the original state, and skin is sutured and closed. According to the above, formation of the thyroid cartilage 11 that can improve vocalization with use of the treatment tool X (treatment for dysphonia) is completed.

Note that when the treatment tool X is fixed between the cut ends 12, 12, to fix the treatment tool X more firmly, a thread may be caused to pass through the hole 3 on the base end side of the front surface contacting section 1d to suture and fix the clamping section 1 and the thyroid cartilage 11 (through the suturing step). In addition, as needed, a thread is also caused to pass through the hole 3 on the distal end side in the longitudinal direction m of the front surface contacting section 1d, and is sutured to the thyroid cartilage 11. Such suturing work can be performed with the clamping sections 1 of the treatment tool X being fitted and temporarily placed between the cut ends 12, 12 of the thyroid cartilage 11.

The treatment tool X set as described above is bent in advance to extend easily along the shape of the thyroid cartilage 11. Hence, an effect of enabling sensory discomfort or strangeness in appearance to be less liable to be caused after the treatment is exerted.

In addition, the front surface contacting section 1d is bent at an angle of equal to or greater than 10 degrees, and hence the bent part functions as a crease. Thus, an effect of enabling the bending angle to be finely adjusted easily at the bent part to extend more securely along the thyroid cartilage 11 is exerted.

In addition, after the treatment, it is conceivable that the clamping pieces of the treatment tool X fixed to the thyroid cartilage oscillate along with vibration of the thyroid cartilage. In this case, when the front surface contacting section 1d is bent with a part overlapping with the hole 3 being as a center, stress is concentrated at a part at which a plate width is reduced due to the hole 3. Hence, there may be a possibility of breakage at the bent part. However, the treatment tool X according to the present invention is bent at a part at which a sufficient plate width is secured between the holes 3, 3. Hence, an effect of enabling avoiding breakage in the periphery of the hole 3 is exerted.

In addition, when the front surface contacting section 1d is bent at an angle of equal to or greater than 50 degrees, the bending angle is greater than a curve angle of the thyroid cartilage 11 of a human, and the front surface contacting section 1d may be required to be bent to return to a direction of obtaining gentle bending. This bending-back acts in a direction of reducing rigidity of the front surface contacting section 1d. However, the bending angle of the front surface contacting section 1d of the treatment tool X is equal to or less than 50 degrees, hence the bending-back can be suppressed to prevent reduction in rigidity of the front surface contacting section 1d.

Note that when the bending angle is equal to or greater than 25 degrees, the crease becomes utilized easily, and an adjusting width is reduced.

In addition, when the bending angle is 30 degrees, the angle is substantially close to an angle of the thyroid cartilage 11 of a female. When the bending angle is 45 degrees, the angle is substantially close to an angle of the thyroid cartilage 11 of a male. Therefore, when the bending angle is equal to and greater than 30 degrees and less than 45 degrees, the treatment tool X is selected regardless of sex, and fine adjustment is performed by utilizing the crease. In this manner, the treatment tool X can be set to the thyroid cartilage 11.

In addition, the part of the front surface piece 1a that is disposed in the front surface 11a of the thyroid cartilage 11 has a thickness dimension set to be equal to or greater than 0.05 mm and equal to or less than 0.6 mm. Hence, an effect of enabling a person to easily bend with use of a jig such as pliers the front surface piece 1a that is rigid and made from titanium at the part bent in advance is exerted.

In addition, the front surface piece 1a is bent to be curved. Hence, an effect of easily fitting in the thyroid cartilage 11 and being less noticeable in appearance is exerted.

Note that in the above embodiment, the example of the treatment tool X in which the two holes 3 are formed in the front surface piece 1a is described; however, the number of the holes 3 is not limited to two, and the number of the holes 3 may be any number or may be zero as along as the clamping of the treatment tool X or the fixing of the treatment tool X is achieved.

In addition, the front surface piece 1a of the treatment tool X according to the present invention may be bent by cutting, casting, or the like at the time of formation, or may be bent by other methods such as a jig after the formation.

Figure 5:
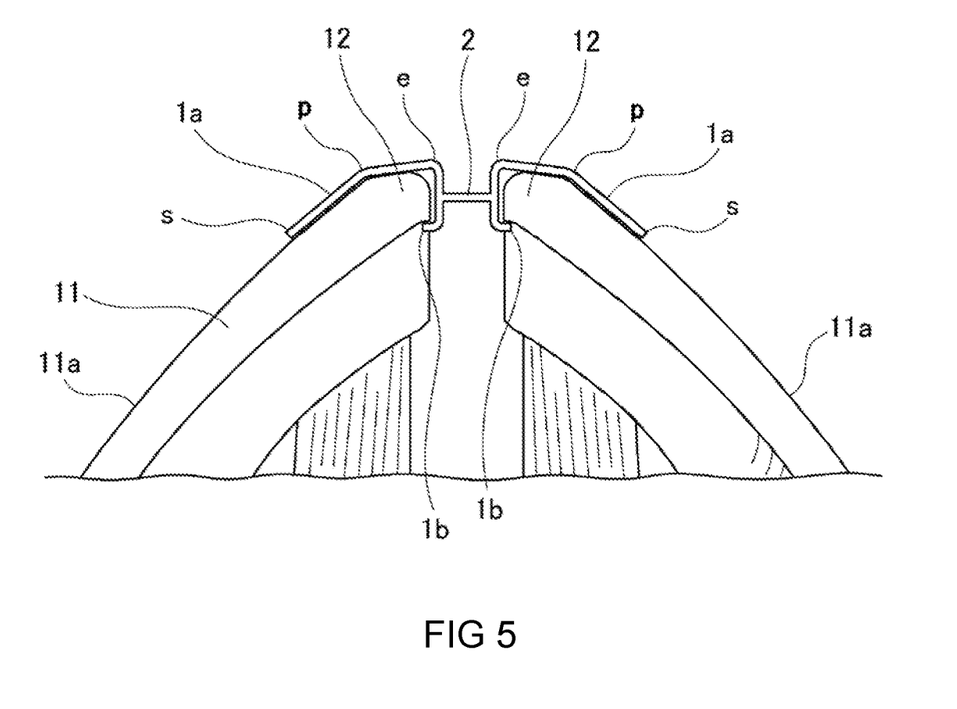
FIG. 5 is a view illustrating a state in which a modified example of the dysphonia treatment tool according to the embodiment of the present invention is set to thyroid cartilage.

In addition, as illustrated in FIG. 5, the treatment tool X according to the present invention may be bent to the rear surface piece 1b side also on the base end e side of the front surface piece 1a, in addition to the position p on the imaginary line L illustrated in FIG. 1.

As described above, the front surface piece 1a is bent at the base end e or the vicinity of the base end e, and at the intermediate section p between the base end e and the distal end s. Thus, an effect of further fitting in the thyroid cartilage 11 is obtained. In addition, when the bending is performed in a stepped manner at the two parts of the base end e or the vicinity of the base end e and the intermediate section p, the bending angle at each part can be reduced. Hence, an effect of enabling reducing a load caused by bending of the treatment tool X to maintain rigidity of the material of the treatment tool X is exerted.

In addition, when only a root part on the base end e side of the front surface piece 1a is bent, a part on the distal end side with respect to the hole 3 on the base end e side floats from the front surface 11a of the thyroid cartilage 11. When the treatment tool X is set to the cut end 12 of the thyroid cartilage 11 under this state, the front surface piece 1a oscillates with the hole 3 on the base end e side being as a fulcrum, and metal fatigue tends to occur. Therefore, as in the present modified example, the front surface piece is bent at the two parts of the base end e of the front surface piece 1a or the vicinity of the base end e and the position p on the imaginary line L, and this is effective in preventing metal fatigue of the front surface piece.

Figure 4:
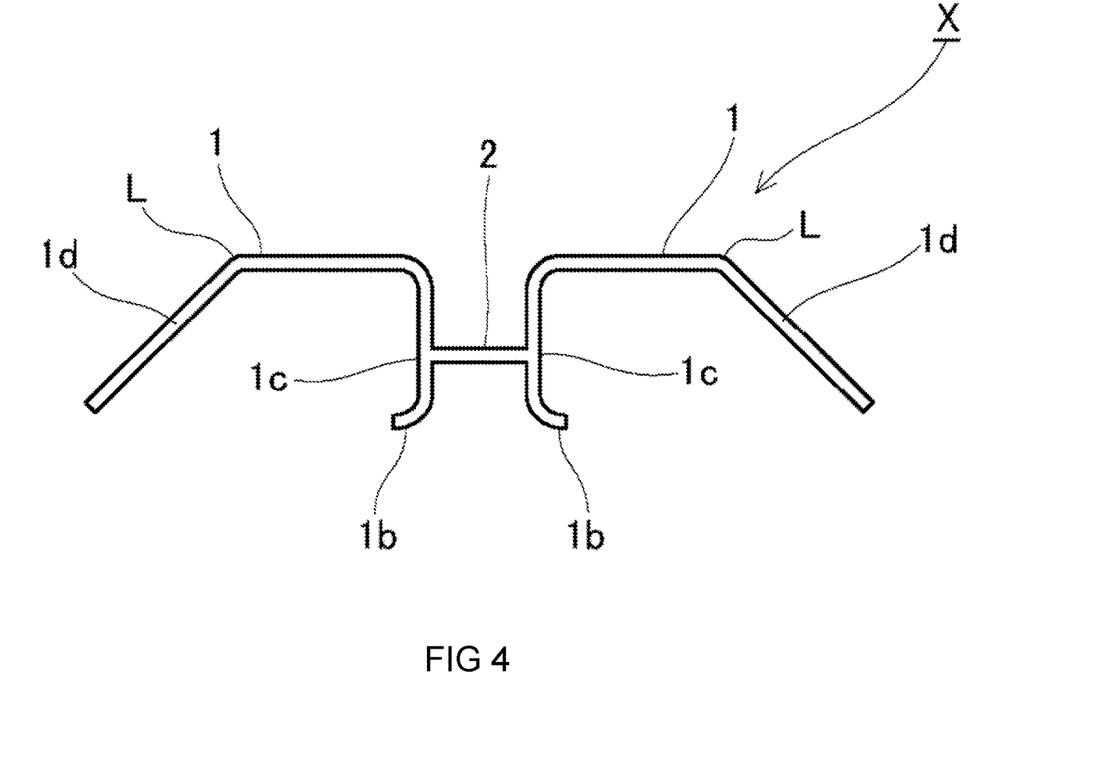
FIG. 4 is a front view illustrating another example of a dysphonia treatment tool according to the present invention.

Further, the front surface piece 1a of the treatment tool X according to the present invention is bent to be curved smoothly. However, the front surface piece 1a may be bent to form a corner portion as illustrated in FIG. 4, that is, to form an angle with a plurality of flat plates, and may be pointed at the center of the bending. According to such a configuration, the bending angle of the front surface piece 1a of the treatment tool X becomes grasped easily.

REFERENCE SIGNS LIST

X Treatment tool (dysphonia treatment tool)
1 Clamping section
1a Front surface piece
1b Rear surface piece
1c End surface section
2 Bridging section
11 Thyroid cartilage
11a Front surface
11b Rear surface
12 Cut end (end portion that is cut)

The invention claimed is:
1. A dysphonia treatment tool comprising:
one or more sets of a pair of clamping sections, wherein one pair of the clamping sections is a set, each of the clamping sections comprising:
a front surface piece in a shape of a strip in a planar view, having in a longitudinal direction of the front surface piece,
a base end side, and
a distal end side, wherein the front surface piece is configured to be disposed from a cut end surface of thyroid cartilage incised to a front surface thereof, and a rear surface piece, the rear surface piece being configured to be disposed on a rear surface of the thyroid cartilage and to be fitted respectively to a cut end of the thyroid cartilage, wherein the cut end faces another cut end; and a bridging section each linking the pair of the clamping sections to each other, wherein a part of the base end side of the front surface piece is bent and forms an end surface section that is configured to be brought into contact with the cut end surface of the thyroid cartilage, and wherein a part of the distal end side of the front surface piece forms a front surface contacting section that is configured to be brought into contact with the front surface of the thyroid cartilage, wherein a plurality of holes is formed in the front surface contacting section of the front surface piece at an interval in the longitudinal direction, wherein the front surface piece is bent toward a side of the rear surface piece in an intermediate section of the front surface contacting section between the distal end side and the base end side of the front surface piece, at a bending portion along an imaginary line passing a substantial center between the plurality of the holes and crossing substantially orthogonally an array direction of the plurality of the holes, so that the front surface piece has a bending angle in a range from 10 degrees to 50 degrees, wherein the bending angle is an angle formed by flat plate portions of the front surface piece, the flat plate portions being adjacent to each other and sandwiching the bending portion of the front surface piece.

2. The dysphonia treatment tool according to claim 1, wherein the part the distal end side of each the front surface piece has a thickness in a range from 0.05 mm to 0.6 mm, and the bending angle of the front surface piece is adjustable within the range from 10 degrees to 50 degrees.

3. The dysphonia treatment tool according to claim 1, wherein each the front surface piece is bent so as to form a corner portion.

4. The dysphonia treatment tool according to claim 1, wherein each the front surface piece is bent at a position at which the imaginary line does not overlap with the plurality of the holes.

5. The dysphonia treatment tool according to claim 4, wherein the imaginary line at which each the front surface piece is bent is located at a center between a pair of the plurality of the holes.

6. The dysphonia treatment tool according to claim 1, wherein each the front surface piece of the pair of the plurality of the clamping sections is linked by the bridging section to another front surface piece of the pair, and the front surface piece is further bent toward the side of the rear surface piece at a side the base end side relative to the intermediate section in which the front surface piece is bent.

\* \* \* \* \*

UNITED STATES PATENT AND TRADEMARK OFFICE
CERTIFICATE OF CORRECTION

| | |
|---|---|
| PATENT NO. | : 11,523,908 B2 |
| APPLICATION NO. | : 16/475318 |
| DATED | : December 13, 2022 |
| INVENTOR(S) | : Isshiki et al. |

It is certified that error appears in the above-identified patent and that said Letters Patent is hereby corrected as shown below:

On the Title Page

Item (22): Delete "Dec. 29, 2016" and insert --Dec. 28, 2017--.

Signed and Sealed this
Fourteenth Day of February, 2023

Katherine Kelly Vidal
*Director of the United States Patent and Trademark Office*